US00PP21001P3

(12) United States Plant Patent
Duncalf

(10) Patent No.: US PP21,001 P3
(45) Date of Patent: May 18, 2010

(54) ***ALSTROEMERIA* PLANT NAMED 'ALSDUN01'**

(50) Latin Name: *Alstroemeria*
Varietal Denomination: AlsDun01

(76) Inventor: Ian Duncalf, 139 Te Puna Road, Tauranga (NZ) RD6

( * ) Notice: Subject to any disclaimer, the term of this patent is extended or adjusted under 35 U.S.C. 154(b) by 0 days.

(21) Appl. No.: 12/228,347

(22) Filed: Aug. 12, 2008

(65) Prior Publication Data

US 2010/0043111 P1 Feb. 18, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner*—Annette H Para
(74) *Attorney, Agent, or Firm*—Fulwider Patton LLP

(57) ABSTRACT

An *Alstroemeria* cultivar particularly distinguished by its bright red flower color, its white flower stems, and its variegated foliage that fades from yellow to white.

1 Drawing Sheet

BACKGROUND

The present invention comprises a new and distinct cultivar of *Alstroemeria*, and hereinafter referred to by the cultivar name 'AlsDun01.' 'AlsDun01' was discovered in approximately 1997 in New Zealand and arose as a sport that arose in tissue culturing of the variety "Red Baron." Red Baron (unpatented) is believed by the inventor not to be protected anywhere in the world at present. The initial trials began in approximately 2001, and the final selection occurred in 2004. Red Baron is an old cut-flower variety that is slightly taller than the present cultivar and has pure dark green foliage and green stems.

'AlsDun01' was selected for its long lasting and striking red flowers, year round growth habit and flowering, white flowering stems, and colorful yellow variegated foliage that fades to white. 'AlsDun01' has been asexually propagated repeatedly by division since 2004 and has been found to retain its distinctive characteristics through successive asexual propagations.

BRIEF DESCRIPTION OF THE PHOTOGRAPH

FIG. 1 shows the overall plant habit and illustrates the variety's mature inflorescences, flower buds, and leaves.

DESCRIPTION OF THE NEW CULTIVAR

The following detailed descriptions set forth the distinctive characteristics of 'AlsDun01'. The data which define these characteristics were collected from asexual reproductions carried out in Tauranga, New Zealand. The data were collected on two year old plants grown under field conditions in full sun. Color references are primarily to The R.H.S. Colour Chart of The Royal Horticultural Society of London (R.H.S.).

DETAILED BOTANICAL DESCRIPTION

Classification:
*Botanical.—Alstroemeria*
Parentage: Red Baron (unpatented).
Plant origin: A sport that arose in tissue culture.

Form: Herbaceous plant arising from an underground rhizome.
Habit: Upright and vigorous.
Plant size: Mature Height 90–100 cm.
Width (spread): Approximately 50 cm.
Flowering habit: Perennial plant
Growth pattern: Stems emerge from underground rhizomes throughout the year with cold and hot temperatures slowing appearance and growth rate.
Flowering: Flowers appear throughout the year but mainly in flushes in Spring and Autumn.
Stem diameter: 6–8 mm
Foliage characteristics: Elliptic to lanceolate, opposite or scattered with a twisted petiole; more lush on growth stems of flowering stems and more lush under lower light levels.
Leaf color: Leaves emerge lime-yellow (center RHS 2C) with a dark green irregular margin (RHS N137B) and age to a creamy white (RHS 158A) with the same dark irregular margin.
Leaf length: 50 to 120 mm (including petiole)
Leaf width: 20 to 40 mm
Flower size: 60 to 70 mm per flower, between 6 and 12 flowers per stem
Bud shape: Ovate
Bud color: Dark Maroon (RHS 59C)
Flower profile (upper): Funnel form
Flower profile (lower): Funnel form
Inflorescence type: Terminal umbel
Sepal: Six clawed tepals, inner three ones narrower
Number of petals: Six tepals
Petal size: Inner tepal 55–65 mm; outer tepal 50–60 mm
Petal width: Inner tepal 15–17 mm; outer tepal 22–25 mm
Petal arrangement: Overlapping
Pedicel length: 22–28 mm (twisted)
Pedicel prickles: none
Number of flowers: 6–12 per flowering stem
Floret length: 60–65 mm
Time of flowering: year round, flush in Spring Flower color midzone outside: Outer tepal RHS 45A & 46A; inner tepal RHS 44A, Stripe RHS 14A, Fleck 165A
Flower color midzone inside: Outer tepal RHS 45A & 46A; inner tepal RHS 44A, Stripe RHS 14A, Fleck 165A
Basal spot color: Cream RHS 158A
Filament color: RHS 45 A
Anther color: RHS 178 B
Style color: RHS 45 A
Growth rate: rapid
Fragrance: none
Spacing: 500–600 mm between plants

COMPARISON WITH PARENTAL AND COMMERCIAL CULTIVARS

'AlsDun01' differs from its closest known variety Red Baron in that Red Baron is slightly taller, slightly more vigorous and had pure dark green foliage rather than the variegated form. The stems of Red Baron are green as opposed to the white stems of 'AlsDun01'.

OTHER CHARACTERISTICS OF THE NEW VARIETY

'AlsDun01' is best suited for temperate conditions but will tolerate both heat and cold. In very cold conditions it will become deciduous. Ideal temperatures range from 15° C.–25° C., where warmer temperatures can slow development of new shoots and flowers. The variety can take full and direct sunlight, but intense sun can cause burning if the plant is dry and full sun can harden the colors. Best environment includes twenty to forty percent shade. Moderate fertilizer levels are adequate for pots, and annual feeds are adequate for ground plants. Soil is ideally free draining and moist. No specific diseases noted, but genus is prone to Cucumber Mosaic Virus.

I claim:

1. A new and distinct cultivar of *Alstroemeria* plant as described and shown herein.

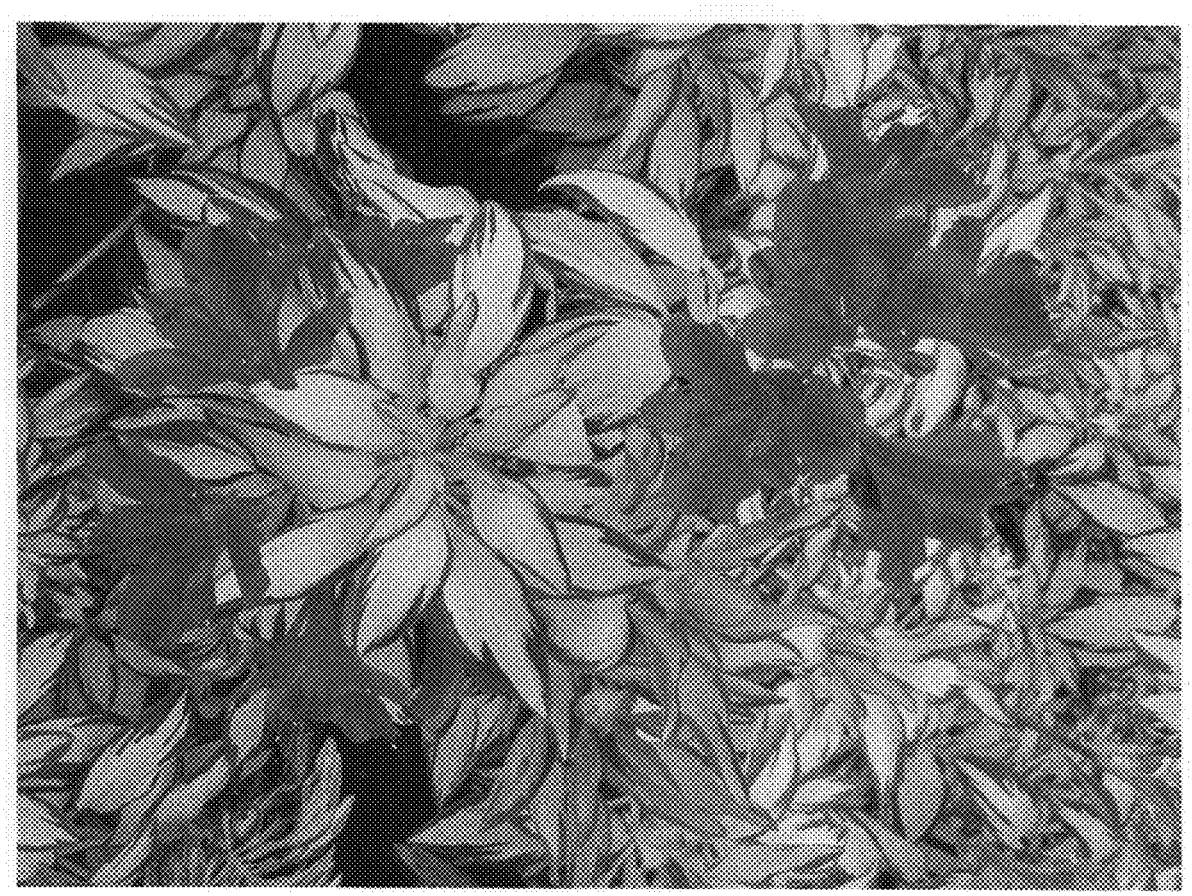

* * * * *